United States Patent [19]

Jones et al.

[11] 4,098,646
[45] Jul. 4, 1978

[54] METHOD OF IN VITRO CULTIVATION OF PATHOGENIC ORGANISMS OF *TREPONEMA PALLIDUM* AND MEDIUM THEREFOR

[75] Inventors: Ronald H. Jones, Melbourne Beach, Fla.; Mary A. Finn, Des Moines, Iowa; John J. Thomas, Satellite Beach; Edward C. Folger, Melbourne, both of Fla.

[73] Assignee: Florida Institute of Technology, Melbourne, Fla.

[21] Appl. No.: 762,920

[22] Filed: Jan. 27, 1977

[51] Int. Cl.² .............................................. C12K 1/06
[52] U.S. Cl. ........................................ 195/96; 195/100
[58] Field of Search ................................ 195/96, 100

[56] References Cited
U.S. PATENT DOCUMENTS 3,502,546  3/1970  Thompson et al. .................. 195/96

*Primary Examiner*—Lionel M. Shapiro
*Attorney, Agent, or Firm*—Omri M. Behr

[57] ABSTRACT

There is provided a tissue cell culture medium for the growth of pathogenic *T. Pallidum* organisms wherein the virulence of said organisms is maintained over many subculture passages.

28 Claims, No Drawings

METHOD OF IN VITRO CULTIVATION OF PATHOGENIC ORGANISMS OF *TREPONEMA PALLIDUM* AND MEDIUM THEREFOR

The work upon which the present application is based was supported in part by grants from the Department of Health, Education and Welfare.

BACKGROUND OF THE INVENTION

The study of the pathogenic organisms, *Treponema pallidum*, which are the organisms responsible for syphilis, has been greatly hampered by the fact that heretofore it has, to all intents and purposes, not been possible to grow and subculture the organisms in vitro while maintaining their virulence. The provision of such a procedure is an important step in developing a vaccine against syphilis in order to avoid antibiotic therapy which, in the case of another venereal disease, gonorrhea, appears to have led to mutant organisms which are resistant to simple antibiotic therapy.

Many attempts have been made heretofore to culture *T. pallidum* in vitro. The first attempts of record are by Schereschewsky reported in Deutsche Medizinische Wochenschrift 35, 835 (1909), ibid. 35, 1260 (1909), ibid. 35, 1652 (1909), ibid. 38, 1315 (1912), and Arch. Derm. Syph (Berl). 200, 456 (1955). Other workers have not been able to repeat this work. Noguchi J. Amer. med. Ass. 57, 102 (1911) and J. exp. Med. 15, 90 (1912) reported the in vitro growth of virulent T. Pallidum in a pure culture medium; however, studies of said cultures received from Noguchi by Levaditi and Danulesco (C. R. Soc. Biol. (Paris) 73, 256 (1912)) reported that the Noguchi cultures were avirulent pathogenic contaminates. Other attempts have been made to culture pathogenic treponemes in vitro using ordinary bacteriological media, tissue culture, or egg culture, but none have been reported as being successful.

SUMMARY OF THE INVENTION

Virulent *t. pallidum* organisms derived from infected rabbits are grown on tissue cell monolayers in a tissue culture medium of predetermined composition comprising salts, amino acids, vitamins, fatty acid and unsaturated fatty acid salts, and, preferably, mannitol and catalase. The efficiency of the medium as a tissue culture medium indicates that optimum results are obtained by subculturing the organisms at approximately 24 hour intervals. The virulence of the organisms thus subcultured is established by the intradermal injection of freshly harvested treponemes into the shaved backs of rabbits.

DESCRIPTION OF THE PREFERRED EMBODIMENTS

There is provided a tissue culture medium (designated hereinafter as TCM-1) comprising certain salts, amino acids, vitamins, and other components in predetermined ratios. While most of these components have heretofore been used in tissue culture media, there provision in the proportions set forth hereinbelow is unsuggested by the art and, in certain cases, use of the components in proportions outside the ranges given is detrimental to optimum yields of virulent *T. pallidum*.

The optimum tissue culture medium (hereinafter TCM-1) for the in vitro growth of virulent pathogenic *T. pallidum* organisms comprises the following components: the solid components of modified Earle's balanced salt solution (W. H. Earle, Nat. Canc. Inst. 4, 167 (1943)) or modified Hank's solution (Proc. Soc. Exp. Biol. Med. 71, 196 (1949)). In the one liter medium solution utilized as the reference solution, there are suitably employed 100 ml of modified Earle's balanced salt solution at a concentration between 9.5 and 17 times that set forth by Earle or 100 ml of modified Hank's solution concentrated to between 6.5 and 12.6 times the standard strength set forth by Hank to provide a concentration of sodium chloride in TCM-1 or TCM-2 of the order of 0.5% to 1% W/V.

There are also employed the solid components of modified Eagle's minimal essential medium (MEM) amino acids without glutamine and modified Eagle'-MEM vitamins (H. Eagle, Science 130, 432 (1959)). There are suitably employed 20 ml of modified Eagle's MEM amino acid solution without glutamine concentrated to between 35 and 65 times the standard strength. It has been found that higher levels of amino acids are toxic to the tissue culture. The solid components of modified Eagle's MEM vitamins are suitably employed as 10 ml of the standard solution concentrated to between 100 and 200 times the normal strength. It has been found that lower levels of vitamin concentration interfere with the proper growth of the *T. pallidum* organisms.

L-glutamine is utilized, preferably at a concentration of between 2.0 and 6.0 mg moles per liter of final solution, concentrations at the lower end of this range being preferred; however, concentrations below the lower level interfere with the efficient growth of *T. pallidum*.

Vitamin $B_{12}$ is employed at concentrations of 0.15 mg through 15 mg per liter of final solution. Biotin is utilized at between 0.1 mg and 1 mg of final solution; however, it has been found that where the alkali metal salts of unsaturated fatty acids, particularly sodium oleate, are constituents of the medium (see below), the amount of biotin utilized may lie at the lower end of the given range.

Cobaltous chloride is utilized at a range of 0.5 to 0.5 milligrams per liter of final solution. The lower end of the range is not critical although some trace of cobaltous chloride in the medium is helpful. On the other hand, unless the vitamin $B_{12}$ component is increased over the range given hereinabove, which is generally not harmful but merely wasteful, a larger amount of cobaltous chloride would be considered as toxic.

It is desirable to utilize bovine serum albumin complexes with saturated and unsaturated fatty acids of between 12 and 22 carbon atoms in the chain. It is especially preferred to utilize oleic acid as the unsaturated component and stearic acid as the saturated component. It is preferred to prepare the complex by adding oleic acid to dilute aqueous sodium hydroxide and adding thereto Earle's base balanced salt solution (hereinafter EBSS) without the calcium and magnesium ion components (the totality hereinafter GKNP). To this mixture is added the requisite amount of bovine serum albumin in the presence of a further amount of GKNP.

The complex between the bovine serum albumin and the salts of the saturated fatty acids are prepared by dissolving the acid in warm aqueous alkali, suitably sodium hydroxide, cooling the solution and adding thereto the bovine serum albumin in GKNP. While these components are separately prepared, in the final TCM-1 or TCM-2 there will be the equivalent of 2 to 40 grams of bovine serum albumin, 5 to 100 milligrams of the alkali metal salt of a mono-unsaturated fatty acid, and 5 to 100 milligrams of the alkali metal salt of a saturated fatty acid of 12 to 22 carbon atoms — all per liter of final solutions.

It has been found that lower levels of the BSA unsaturated fatty acid salt complexes do not permit *T. pallidum* growth while higher levels are toxic to the tissue culture. With respect to the BSA saturated fatty acid salt complexes, both higher and lower levels are toxic to the tissue culture.

There may also be employed mannitol and catalase. Mannitol may be present in amounts up to 1% by weight of the final medium, preferably between 1 and 10 grams per liter of TCM-1. Catalase may be utilized at between 3 times $10^5$ and 1 times $10^6$ units per liter of TCM-1. It has been found that while *T. pallidum* will grow in a medium devoid of mannitol or catalase (hereinafter TCM-2), reduction of these two components below the stated level appears to negatively affect the virulence of the *T. pallidum* organisms. Except for the ommission of mannitol and catalase, the composition range of TCM-2 is the same as that of TCM-1 set forth above.

There is also employed a sufficient amount of distilled water to bring the foregoing solid and solutioned components up to a total standard of volume of 1 liter. The invention is not, of course, limited to solutions of 1 liter; however, it has been found convenient to express the mutual proportions and dilutions of the various components in terms of a tissue culture medium solution having a volume of 1 liter.

To the foregoing tissue culture medium, there may also be added an inorganic buffer. The amount of inorganic buffer is not critical provided that a pH level of 7.0 to 7.8 pH units is maintained. It is not desirable to utilize organic buffers such as tris or HEPES which negatively affect the growth of *T. pallidum* organisms. Among the most readily available and preferred inorganic buffers may be mentioned sodium bicarbonate.

If desired, the pH of the tissue culture medium may be indicated by the presence of phenol red as an indicator. This indicator, of course, has no positive function in the tissue culture medium with respect to the growth of the cells or the organism; however, the amount of phenol red should not exceed 10 milligrams per liter of TCM-1 or TCM-2 since higher amounts have a toxic effect.

The issue culture is prepared using tissue cells, suitably baby hamster kidney cells, cultured in Eagle's minimal essential medium (MEM) including Earle's balanced salt solution and supplemented to contain 10% fetal calf serum (hereinafter FCS). It has been found useful to grow the *T. pallidum* on cell culture mono layers. For this purpose, the cells from the routine culture are washed in EBSS lacking calcium and magnesium salt ions (GKNP), resuspended in MEM-2% FCS. The tissue culture plates to be used for growth purposes are then inoculated with a suspension of the thus prepared tissue cells. It has been found suitable to utilize approximately 3 times $10^{+4}$ tissue cells per ml of suspension.

The cell cultures are incubated for from about 8 to about 18 hours at from about 16 to about 38° C, suitably from about 27° to 35° C, most suitably 33° C, in an aerobic atmosphere containing between 0 to 10%, preferably between 3 and 8%, most suitably 7%, of carbon dioxide. After incubation, the medium is decanted and the cell mono layers washed with GKNP. A volume of the tissue culture medium, suitably TCM-1, in volume equivalent to the volume of tissue cell suspension initially inoculated into the tissue culture plates is added to the cells, the cultures reincubated for from about 18 to about 30, suitably about 24, hours. The medium is then decanted, the cells washed again with GKNP, and a further, similar amount, of tissue culture medium, suitably TCM-1, added, and the cells incubated a further 18 to 24 hours until the mono layers were observed as 2 plus on a 1 to 4 plus mono layer growth confluency scale. The medium is yet again decanted, the cell mono layers washed yet again with GKNP, and a volume of tissue culture medium, suitably TCM-1, similar to that utilized hereinbefore, containing freshly harvested organisms of *T. pallidum* is added to the cells having an initial confluency of 1.5 – 2.5. The amount of *T. pallidum* organisms utilized is not critical and may, suitably, lie between $10^4$ and $10^7$ organisms per ml. It has been found suitable, however, to inject about $10^5$ treponemes per ml. The inoculated cultures are then incubated as set forth hereinabove for the uninfected cell cultures and the treponemes harvested after approximately 24 hours.

It has been found that where the organisms are permitted to grow in a given culture for more than about 24 hours, the the tissue cells will usually lyse.

The organisms harvested from a given batch produced as hereinabove are diluted to a suspension of the order of $10^5$ organisms per ml, and similarly subcultured in previously uninfected cell mono layers prepared as hereinabove.

It has been found that virulence has been maintained in this manner in up to eight generations of subculture. In similar experiments utilizing a tissue culture medium (TCM-2) which did not contain mannitol and catalase, virulence was not observed past the fifth subculture generation.

STRENGTH RANGES OF STANDARD SOLUTIONS

The modified Earle's balanced salt solution has the following ranges of final standard strength:

|  | mg/l |
|---|---|
| NaCl | 5557.5 – 9945 |
| KCl | 380 – 680 |
| $NaH_2PO_4 \cdot H_2O$ | 133 – 238 |
| $MgSO_4 \cdot 7H_2O$ | 190 – 340 |
| $CaCl_2$ | 190 – 340 |
| Glucose | 950 – 1700 |

The modified Hank's balanced salt solution has the following ranges of final standard strength:

|  | mg/l |
|---|---|
| $CaCl_2$ | 91 – 176.4 |
| KCl | 260 – 504 |
| $KH_2PO_4$ | 39 – 75.6 |
| $MgCl_2 \cdot 6H_2O$ | 65 – 126 |
| $MgSO_4 \cdot 7H_2O$ | 65 – 126 |
| NaCl | 5200 – 10,080 |
| $NaHCO_3$ | 227.5 – 441 |
| $Na_2HPO_4 \cdot 2H_2O$ | 39 – 75.6 |
| Glucose | 650 – 1,260 |

The modified Eagle's amino acid solution without glutamine has the following ranges of final standard strength:

|  | mg/l |
|---|---|
| L-Arginine | 73.5 – 136.5 |
| L-Cystine | 16.8 – 31.2 |

-continued

| | mg/l |
|---|---|
| L-Histidine | 21.7 – 40.3 |
| L-Isoleucine | 36.75 – 68.25 |
| L-Leucine | 36.68 – 68.12 |
| L-Lysine | 40.6 – 75.4 |
| L-Methionine | 10.5 – 19.5 |
| L-Phenylalanine | 22.4 – 41.6 |
| L-Threonine | 33.6 – 62.4 |
| L-Tryptophan | 7 – 13 |
| L-Tyrosine | 25.2 – 46.8 |
| Valine | 32.2 – 59.8 |

The modified Eagle's MEM vitamin solution has the following ranges of final standard strength:

| | mg/l |
|---|---|
| Choline Cl | 1 – 2 |
| Folic acid | 1 – 2 |
| i-Inositol | 2 – 4 |
| Nicotinamide | 1 – 2 |
| D-Ca pantothenate | 1 – 2 |
| Pyridoxal HCl | 1 – 2 |
| Riboflavin | 0.1 – .2 |
| Thiamine | 1.0 – 2 |

All the foregoing four solutions are expressed in terms of milligrams per liter (mg/l).

METHOD OF DETERMINING VIRULENCE OF HARVESTED ORGANISM

A standard curve between the time of lesion development and the serial numbers of freshly harvested treponemes injected intradermally (ID) on each side of shaved backs of rabbits was determined from three different experiments. Each level of treponemes was injected into a total of six rabbits representing twelve sites of inoculation. Times of lesion development are charted as an arithmetic means for each cell number injected.

From each subculture, supernatant fluid and cell-associated treponemes were combined and adjustments made with fresh TCM-1 or TCM-2 to provide 0.1 ml. volumes containing $10^5$ and $10^3$ (motile plus non-motile) treponemes, respectively. Each inoculum level was injected intradermally on each side of a shaved back of one or both of two female rabbits as indicated. The inoculated sites were monitored daily and time of lesion development recorded and compared to the standard curve for estimating number of virulent organisms injected. The presence of treponemes in developed lesions was confirmed by darkfield microscopy. As controls, uninfected tissue cells incubated for 24 hours were harvested and cell numbers adjusted with TCM-1 or TCM-2 so as to be comparable to that of the infected cells injected into rabbits. Volumes of 0.1 ml. of the respective adjusted numbers of uninoculated cells were injected twice intradermally on the shaven backs of each of two female rabbits. All injected animals were maintained in an environmental temperature of 20° C or less.

FORMULATION OF A PREFERRED TISSUE CULTURE MEDIUM (TCM-1)

| TISSUE CULTURE MEDIUM 1 (TCM-1) | | |
|---|---|---|
| Ingredients | ml. | Source |
| Earle's balanced salt solution (10×) | 100.0 | a |
| Eagle's MEM amino acids (50 ×) without glutamine | 20.0 | a |
| Eagle's MEM vitamins (100 ×) | 10.0 | a |
| Glutamine (200 mM) (100 ×) | 10.0 | a |
| Vitamin $B_{12}$ (150 ug./ml.) (1,000 ×) | 1.0 | b |
| Biotin (100 ug./ml.) (1,000 ×) | 1.0 | b |
| Cobalt chloride (0.5 ug./ml.) (100 ×) | 10.0 | c |
| $NaHCO_3$ (7 per cent) | 17.5 | c |
| BSA-Na oleate complex | 40.0 | d |
| BSA-Na stearate complex | 65.0 | c** |
| Phenol red (0.5 per cent) | 12.5 | c |
| Mannitol (10 per cent) | 100.0 | c* |
| Catalase (32,000 units/ml.) | 10.0 | e* |
| Distilled water (Triple glass distilled) | 603.0 | |
| Total | 1,000.0 | | a = International Scientific Industries (Cary, Ill.)
b = Sigma (St. Louis, Mo.)
c = Mallinckrodt (St. Louis, Mo.); c** = stearic acid
d = Bovine serum albumin, Pentex fr. V, lipid poor, Lot 27 (Miles Labs., South Bend, Ind.) Oleic acid (Hormel Institute, Austin, Minn.)
e = Worthington (Freehold, N.J.)
*TCM-1 less mannitol and catalase = TCM-2

RESULT OF VIRULENCE TEST OF T. PALLIDUM CELLS SUBCULTURED IN TWO TISSUE CULTURE SYSTEMS

| Subculture | | | Concurrent Experiments A (TCM-1) | | | | |
|---|---|---|---|---|---|---|---|
| Hrs after | | | No. of treponemes inoculated | | | | |
| No. | Harvest | Animal | $10^5$ | Day[a] | ENVT | $10^3$ | Day | ENVT |
| 0 | 24 | 1 | 0/2[b] | | | 0/2 | | |
| | | 2 | 0/2 | | | 0/2 | | |
| 1 | 48 | 1 | 2/2 | 4 | $10^7$ | 0/2 | | |
| | | 2 | 2/2 | 4 | $10^7$ | 0/2 | | |
| 2 | 72 | 1 | 0/2 | | | 0/2 | | |
| | | 2 | 0/2 | | | 0/2 | | |
| 3 | 96 | 1 | 0/2 | | | 0/2 | | |
| | | 2 | 0/2 | | | 0/2 | | |
| 4 | 120 | 1 | 2/2 | 7 | $6 \times 10^5$ | 0/2 | | |
| 5 | 144 | 1 | 2/2 | 8 | $10^5$ | 0/2 | | |
| 6 | 168 | — | ND | | | ND | | |
| 7 | 192 | 1 | 2/2 | 6 | $10^6$ | 2/2 | 9 | $6 \times 10^4$ |
| 8 | 216 | 1 | 2/2 | 6 | $10^6$ | 2/2 | 9 | $6 \times 10^4$ |
| 9 | 240 | 1 | 0/2 | | | 0/2 | | |

| Subculture | | | Concurrent Experiments B (TCM-2) | | | | |
|---|---|---|---|---|---|---|---|
| Hrs after | | | No. of treponemes inoculated | | | | |
| No. | harvest | Animal | $10^5$ | Day | ENVT | $10^3$ | Day | ENVT |
| 0 | 24 | 1 | 0/2 | | | 0/2 | | |
| | | 2 | 0/2 | | | 0/2 | | |
| 1 | 48 | 1 | 2/2 | 6 | $10^6$ | 2/2 | 10 | $10^4$ |
| | | 2 | 2/2 | 6 | $10^6$ | 0/2 | | |
| 2 | 72 | 1 | 0/2 | | | 0/2 | | |
| | | 2 | ND[c] | | | ND | | |
| 3 | 96 | 1 | 0/2 | | | 0/2 | | |
| | | 2 | ND | | | ND | | |
| 4 | 120 | 1 | 0/2 | | | 0/2 | | |
| 5 | 144 | 1 | 2/2 | 7 | $6 \times 10^5$ | 0/2 | | |
| 6 | 168 | — | ND | | | ND | | |
| 7 | 192 | 1 | ND | | | ND | | |
| 8 | 216 | 1 | 0/2 | | | 0/2 | | |
| 9 | 240 | 1 | 0/2 | | | 0/2 | | |

[a] Day of lesion appearance
[b] Number of sites having developed lesions/number of sites injected intradermally
ENVT = estimated number of virulent treponemes in 0.1 ml. inoculum, based on time of lesion appearance
[c] ND = not done

We claim:
1. A tissue culture medium suitable for the growth of pathogenic organisms of *Treponema Pallidum* in the presence of cultured tissue cells wherein one liter of said medium comprises the solid components of:
   (a) 100 ml of a balanced salt solution selected from modified Earle's balanced salt solution concentrated to between 9.5 and 17 times the standard strength and modified Hank's balanced salt solution concentrated to between 6.5 and 12.6 times standard strength,

(b) 20 ml of modified Eagle's MEM amino acid solution without glutamine concentrated to between 35 and 65 times standard strength, and
(c) 10 ml of modified Eagle's MEM vitamin solution concentrated to between 100 and 200 times standard strength wherein the modified Earle's balanced salt solution has the following ranges of final standard strength:

|  | mg/l |
|---|---|
| NaCl | 5557.5 – 9945 |
| KCl | 380 – 680 |
| $NaH_2PO_4 \cdot H_2O$ | 133 – 238 |
| $MgSO_4 \cdot 7H_2O$ | 190 – 340 |
| $CaCl_2$ | 190 – 340 |
| Glucose | 950 – 1700 | the modified Hank's balanced salt solution has the following ranges of final standard strength:

|  | mg/l |
|---|---|
| $CaCl_2$ | 91 – 176.4 |
| KCl | 260 – 504 |
| $KH_2PO_4$ | 39 – 75.6 |
| $MgCl_2 \cdot 6H_2O$ | 65 – 126 |
| $MgSO_4 \cdot 7H_2O$ | 65 – 126 |
| NaCl | 5200 – 10,080 |
| $NaHCO_3$ | 227.5 – 441 |
| $Na_2HPO_4 \cdot 2H_2O$ | 39 – 75.6 |
| Glucose | 650 – 1,260 | the modified Eagle's amino acid solution without glutamine has the following ranges of final standard strength:

|  | mg/l |
|---|---|
| L-Arginine | 73.5 – 136.5 |
| L-Cystine | 16.8 – 31.2 |
| L-Histidine | 21.7 – 40.3 |
| L-Isoleucine | 36.75 – 68.25 |
| L-Leucine | 36.68 – 68.12 |
| L-Lysine | 40.6 – 75.4 |
| L-Methionine | 10.5 – 19.5 |
| L-Phenylalanine | 22.4 – 41.6 |
| L-Threonine | 33.6 – 62.4 |
| L-Tryptophan | 7 – 13 |
| L-Tyrosine | 25.2 – 46.8 |
| Valine | 32.2 – 59.8 | and the modified Eagle's MEM vitamin solution has the following ranges of final standard strength:

|  | mg/l |
|---|---|
| Choline Cl | 1 – 2 |
| Folic acid | 1 – 2 |
| i-Inositol | 2 – 4 |
| Nicotinamide | 1 – 2 |
| D-Ca pantothenate | 1 – 2 |
| Pyridoxal HCl | 1 – 2 |
| Riboflavin | 0.1 – .2 |
| Thiamine | 1.0 – 2 | all the foregoing four solutions being expressed in terms of milligrams per liter (mg/l) and,
said medium further comprising:
(d) L-Glutamine, 2 – 6.0 mg mols
(e) Vitamin $B_{12}$, 0.15 mg to 15 mg,
(f) Biotin, 0.1 mg to 1.0 mg,
(g) Cobaltous Chloride, 0.05 mg to 0.5 mg,
(h) an alkali metal salt of a mono-unsaturated fatty acid of 12 to 22 carbon atoms, 5 mg to 100 mg,
(i) an alkali metal salt of a saturated fatty acid of 12 to 22 carbon atoms, 5 to 100 mg,
(j) Bovine serum albumin 4 grams to 40 grams,
(k) Mannitol, 1 gram to 10 grams,
(l) Catalase, 3 times $10^5$ units to 1 times $10^6$ units,
and distilled water to dilute all of said foregoing components up to 1 liter of medium.

2. A medium of claim 1 wherein the salt solution is Earle's balanced salt solution of between 9.5 and 17 times standard strength.

3. A medium of claim 2 additionally comprising an inorganic buffer in an amount proper to maintain the pH of the medium between 7.0 and 7.8 pH units.

4. A medium according to claim 3 wherein the buffer is sodium bicarbonate.

5. A medium according to claim 2 wherein the unsaturated acid is oleic acid.

6. A medium according to claim 2 wherein the saturated acid is stearic acid.

7. A medium according to claim 1 hwerein the salt solution is Hank's adjusted salt solution concentrated to between 6.5 and 12.5 times standard strength.

8. A medium according to claim 7 additionally comprising an inorganic buffer in an amount proper to maintain the pH of the medium between 7.0 and 7.8.

9. A medium according to claim 8 wherein the buffer is sodium bicarbonate.

10. A medium according to claim 7 wherein the unsaturated acid is oleic acid.

11. A medium according to claim 7 wherein the saturated acid is stearic acid.

12. A method of culturing pathogenic organisms of *T. pallidum* while maintaining the virulence thereof which comprises:
(I) inoculating *T. pallidum* into a tissue culture medium comprising:
(a) the medium of claim 1,
(b) a sufficient number of tissue cells to provide a monolayer having an initial confluency in the medium of 1.5 to 2.5 on a confluency scale of 1 through 4,
(II) incubating said inoculated culture for up to 24 hours at a temperature between 16 and 38° C in an aerobic atmosphere containing 0 through 10% of carbon dioxide,
(III) harvesting the *T. pallidum* organisms.

13. A method of claim 12 wherein the organisms are incubated at a temperature between 27° through 35° C in an aerobic atmosphere containing 3 to 8% of carbon dioxide.

14. A process of claim 12 additionally comprising sub-culturing a portion of the harvest of step (III) of claim 12 in accordance with the procedures of steps (I) and (II) of Claim 12 and the harvesting the organisms and continuing said sub-culturing of said organisms as frequently as desired.

15. A tissue culture medium suitable for the growth of pathogenic organisms of *Treponema pallidum* in the presence of cultured tissue cells wherein one liter of said medium comprises the solid components of:
(a) 100 ml of a balanced salt solution selected from modified Earle's balanced salt solution concentrated to between 9.5 and 17 times the standard strength and modified Hank's balanced salt solution concentrated to between 6.5 and 12.6 times standard strength, (b) 20 ml of modified Eagle's MEM amino acid solution without glutamine concentrated to between 35 and 65 times standard strength, and (c) 10 ml of modified Eagle's MEM vitamin solution concentrated to between 100 and 200 times standard strength wherein the modified Earle's balanced salt solution has the following ranges of final standard strength:

| | mg/l |
|---|---|
| NaCl | 5557.5 – 9945 |
| KCl | 380 – 680 |
| NaH$_2$PO$_4$ . H$_2$O | 133 – 238 |
| MgSO$_4$ . 7H$_2$O | 190 – 340 |
| CaCl$_2$ | 190 – 340 |
| Glucose | 950 – 1700 | the modified Hank's balanced salt solution has the following ranges of final standard strength:

| | mg/l |
|---|---|
| CaCl$_2$ | 91 – 176.4 |
| KCl | 260 – 504 |
| KH$_2$PO$_4$ | 39 – 75.6 |
| MgCl$_2$ . 6H$_2$O | 65 – 126 |
| MgSO$_4$ . 7H$_2$O | 65 – 126 |
| NaCl | 5200 – 10,080 |
| NaHCO$_3$ | 227.5 – 441 |
| Na$_2$HPO$_4$ . 2H$_2$O | 39 – 75.6 |
| Glucose | 650 – 1,260 | the modified Eagle's amino acid solution without glutamine has the following ranges of final standard strength:

| | mg/l |
|---|---|
| L-Arginine | 73.5 – 136.5 |
| L-Cystine | 16.8 – 31.2 |
| L-Histidine | 21.7 – 40.3 |
| L-Isoleucine | 36.75 – 68.25 |
| L-Leucine | 36.68 – 68.12 |
| L-Lysine | 40.6 – 75.4 |
| L-Methionine | 10.5 – 19.5 |
| L-Phenylalanine | 22.4 – 41.6 |
| L-Threonine | 33.6 – 62.4 |
| L-Tryptophan | 7 – 13 |
| L-Tyrosine | 25.2 – 46.8 |
| Valine | 32.2 – 59.8 | and the modified Eagle's MEM vitamin solution has the following ranges of final standard strength:

| | mg/l |
|---|---|
| Choline Cl | 1 – 2 |
| Folic acid | 1 – 2 |
| i-Inositol | 2 – 4 |
| Nicotinamide | 1 – 2 |
| D-Ca pantothenate | 1 – 2 |
| Pyridoxal HCl | 1 – 2 |
| Riboflavin | 0.1 – .2 |
| Thiamine | 1.0 – 2 | all the foregoing four solutions being expressed in terms of milligrams per liter (mg/l)
and,
said medium further comprising:

(d) L-Glutamine, 2 - 6.0 mg mols
(e) Vitamin B$_{12}$, 0.15 mg to 15 mg,
(f) Biotin, 0.1 mg to 1.0 mg,
(g) Cobaltous Chloride, 0.05 mg to 0.5 mg,
(h) an alkali metal salt of a mono-unsaturated fatty acid of 12 to 22 carbon atoms, 5 mg to 100 mg,
(i) an alkali metal salt of a saturated fatty acid of 12 to 22 carbon atoms, 5 to 100 mg,
(j) Bovine serum albumin 4 grams to 40 grams, and distilled water to dilute all of said foregoing components up to 1 liter of medium.

16. A medium of claim 15 wherein the salt solution is Earle's balanced salt solution of between 9.5 and 17 times standard strength.

17. A medium of claim 16 additionally comprising an inorganic buffer in an amount proper to maintain the pH of the medium between 7.0 and 7.8 pH units.

18. A medium according to claim 17 wherein the buffer is sodium bicarbonate.

19. A medium according to claim 16 wherein the unsaturated acid is oleic acid.

20. A medium according to claim 16 wherein the saturated acid is stearic acid.

21. A medium according to claim 15 hwerein the salt solution is Hank's adjusted salt solution concentrated to between 6.5 and 12.5 times standard strength.

22. A medium according to claim 21 additionally comprising an inorganic buffer in an amount proper to maintain the pH of the medium between 7.0 and 7.8 pH units.

23. A medium according to claim 22 wherein the buffer is sodium bicarbonate.

24. A medium according to claim 21 wherein the unsaturated acid is oleic acid.

25. A medium according to claim 21 wherein the saturated acid is stearic acid.

26. A method of culturing pathogenic organisms of *T. Pallidum* while maintaining the virulence thereof which comprises:

I) inoculating *T. pallidum* into a tissue culture medium system comprising:
(a) the medium of claim 15,
(b) a sufficient number of tissue cells to provide a mono layer having an initial confluency in the medium of 1.5 to 2.5 on a confluency scale of 1 through 4,
(II) incubating said inoculated culture for up to 24 hours at a temperature of between 16° and 38° C in an aerobic atmosphere containing 0 through 10% of carbon dioxide,
III) harvesting the *T. pallidum* organisms.

27. A method of claim 26 wherein the organisms are incubated at a temperature of between 16° through 38° C in an aerobic atmosphere containing 0 to 10% of carbon dioxide.

28. A process of claim 26 additionally comprising sub-culturing a portion of the harvest of step (III) of claim 26 in accordance with the procedures of steps (I) and (II) of claim 26 and then harvesting the organisms and continuing sub-culturing of said organisms as frequently as desired.

* * * * *